(12) United States Patent
Ting (10) Patent No.: US 8,939,251 B2
(45) Date of Patent: Jan. 27, 2015

(54) STETHOSCOPE WITH LIGHT SOURCE AND/OR TIMEPIECE

(71) Applicant: MDF Instruments USA, Inc., Agoura Hills, CA (US)

(72) Inventor: Darren Talun Chiao Ting, Malibu, CA (US)

(73) Assignee: MDF Instruments USA, Inc., Westlake Village, CA (US)

( * ) Notice: Subject to any disclaimer, the term of this patent is extended or adjusted under 35 U.S.C. 154(b) by 0 days.

(21) Appl. No.: 13/929,420

(22) Filed: Jun. 27, 2013

(65) Prior Publication Data

US 2014/0005574 A1    Jan. 2, 2014

Related U.S. Application Data

(60) Provisional application No. 61/665,257, filed on Jun. 27, 2012.

(51) Int. Cl.
*A61B 7/02* (2006.01)

(52) U.S. Cl.
USPC .......................................... 181/131; 600/586

(58) Field of Classification Search
CPC ......................................................... A61B 7/02
USPC .......................................... 181/131; 600/586
See application file for complete search history.

(56) References Cited

U.S. PATENT DOCUMENTS

| 4,239,089 A | 12/1980 | Nelson |
| 4,669,572 A | 6/1987 | Fassbender |
| 4,802,550 A * | 2/1989 | Poore ............................ 181/131 |
| 5,022,487 A | 6/1991 | Kirchner |
| 5,252,787 A * | 10/1993 | Moore et al. ................... 181/131 |
| 5,389,747 A * | 2/1995 | Mohrin ......................... 181/131 |

(Continued)

FOREIGN PATENT DOCUMENTS

CN    202235434 U    5/2012

OTHER PUBLICATIONS

Derwent abstract for CN103536311, STtehoscope, has chest piece whose upper part is provided with electronic thermometer that is provided with display device and temperature probe, where chest piece is connected with buckle cover through rotating chaft, all pages pertinent.*
MDF Instruments Stethoscope Collection Brochure, dated May 10, 2011.

(Continued)

*Primary Examiner* — Forrest M Phillips
(74) *Attorney, Agent, or Firm* — The Law Office of Patrick F. O'Reilly III, LLC (57) ABSTRACT

A stethoscope with a built-in light and/or a timepiece powered with a power source subassembly for examining patients' vital signs is disclosed. The stethoscope includes a chestpiece assembly with a diaphragm component, a light source subassembly, a switch subassembly which is operatively connected to the light source subassembly and controls the off and on position of a light emitting element. In some embodiments, the chestpiece assembly of the stethoscope further includes a timepiece subassembly to measure time during a vital sign examination. The switch subassembly of chestpiece assembly is configured to provide operational control of the current flow from the power source subassembly to the light emitting element as well as control over the acoustic valve subassembly that would inhibit or permit the transmission of sound waves from the diaphragm through the acoustic tube.

20 Claims, 5 Drawing Sheets

(56) References Cited

U.S. PATENT DOCUMENTS

| | | | |
|---|---|---|---|
| 6,202,784 B1* | 3/2001 | Alatriste | 181/131 |
| 6,454,045 B1* | 9/2002 | Ryan | 181/131 |
| 6,932,186 B2 | 8/2005 | Costa et al. | |
| 7,036,627 B2* | 5/2006 | Costa et al. | 181/131 |
| 2008/0245602 A1* | 10/2008 | Nakamura | 181/131 |
| 2010/0155173 A1* | 6/2010 | Boyd et al. | 181/131 |

OTHER PUBLICATIONS

MDF Instruments Product Brochure, dated earlier than Apr. 2012 (exact date unknown).

MDF Instruments ProCardial Stethoscope Brochure, dated Apr. 4, 2012.

MDF Instruments Cardio-X Stethoscope Brochure, dated Mar. 15, 2012.

* cited by examiner

STETHOSCOPE WITH LIGHT SOURCE AND/OR TIMEPIECE

CROSS-REFERENCE TO RELATED APPLICATIONS

This patent application claims priority to, and incorporates by reference in its entirety, U.S. Provisional Patent Application No. 61/665,257, entitled "Stethoscope With Light Source And Timepiece", filed on Jun. 27, 2012.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to stethoscopes and more particularly to a stethoscope having a light suitable for patient examination and a readily accessible time source when needed to improve monitoring patients during general examination.

2. Background and Description of Related Art

It is known in the art that a medical practitioner employs various devices during the course of examination of a patient. One such instrument is a stethoscope that is used by physicians, nurses, and paramedics in the early stage of any general examination and/or proper vital sign examination of a patient.

A stethoscope is an acoustic medical device for auscultation, or listening to the internal sounds of a body. It is often used to listen to heart sounds. It is also used to listen to intestines and blood flow in arteries and veins. Acoustic stethoscopes operate on the transmission of sounds from the chestpiece, via air-filled hollow tubes, to a binaural (headset) that a practitioner uses to listen to the acoustic sounds of a patient. The chestpiece usually consists of a diaphragm and a housing that supports the diaphragm within the chestpiece body. When the diaphragm is placed on the patient, body sounds vibrate the diaphragm, creating acoustic pressure waves which travel up the tubing to the binaural and the listener's ears.

The proper operation of a stethoscope is essential, since a practitioner, nurse or a doctor, uses a stethoscope to listen to the sounds of a patient's body to determine normal functioning and abnormalities.

In addition to stethoscopes, medical practitioners may use flash lights to examine the eyes of a patient for pupil dilation and reaction and/or use a time measurement device that would allow them to monitor a patient's heart or breathing rate. These additional instruments may be stored at various examination stations and may not be accessible in a timely manner by practitioners when needed. As such, a crucial part of the vital sign exams may be missed simply because clinicians do not have the proper tools in their possession. For example, clinicians may not conduct a pupillary response evaluation because they do not have a light handy, or may miss monitoring the heart rate because they do not have a time measuring device in their possession.

Therefore, what is needed is a multi-functional instrument including a plurality of devices that could be utilized by a medical practitioner to conduct a proper vital sign examination of a patient in a timely manner. Moreover, an instrument is needed that enables clinicians to easily conduct the crucial vital sign examination as a part of all general examinations. Furthermore, what is needed is an instrument that permits a clinician to check a plurality of the patient's vital signs without necessitating the removal of multiple instruments.

BRIEF SUMMARY OF EMBODIMENTS OF THE INVENTION

Accordingly, the present invention is directed to a stethoscope with a light source and/or a timepiece that substantially obviates one or more problems in the related art hereinbefore discussed.

In accordance with one aspect of one or more embodiments of the present invention, there is provided a stethoscope that includes a binaural assembly with an acoustic tube and a stethoscope chestpiece assembly. The stethoscope chestpiece assembly includes a chestpiece body having a first end and a second end; a diaphragm attached to the first end of the chestpiece body; a light source subassembly coupled to the chestpiece body, the light source subassembly including a light emitting element for performing a vital sign examination; a switch subassembly operatively coupled to the light source subassembly for turning the light emitting element on and off; a power source subassembly including a power source, the power source subassembly operatively connected to the light source subassembly; and a rotatable acoustic valve disposed in the chestpiece body, the rotatable acoustic valve being fluidly coupled with the acoustic tube of the binaural assembly, and the rotatable acoustic valve being configured to regulate the transmission of sound waves through the binaural assembly.

In accordance with another aspect of one or more embodiments of the present invention, there is provided a stethoscope that includes a binaural assembly with an acoustic tube and a stethoscope chestpiece assembly. The stethoscope chestpiece assembly includes a chestpiece body having a first end and a second end; a diaphragm attached to the first end of the chestpiece body; a light source subassembly coupled to the chestpiece body, the light source subassembly including a light emitting element for performing a vital sign examination; a switch subassembly operatively coupled to the light source subassembly for turning the light emitting element on and off, the switch subassembly including a rotatable acoustic valve; and a power source subassembly including a power source, the power source subassembly operatively connected to the light source subassembly. In this embodiment, the rotatable acoustic valve is fluidly coupled with the acoustic tube of the binaural assembly, the rotatable acoustic valve being configured to regulate the transmission of sound waves through the binaural assembly.

In a further embodiment of this aspect of the present invention, the light source subassembly further comprises: a socket disposed within a cavity of the chestpiece body, the socket having a mouth; and a transparent dome-shaped cover disposed over the mouth of the socket. In this further embodiment, the light emitting element is disposed in the socket, the light emitting element configured to emit light in response to being energized by power supplied from the power source.

In yet a further embodiment, the switch subassembly further comprises: a positive adherent point element coupled to a positive connecting sheet, the positive connecting sheet engageable with the power source subassembly for turning the light emitting element on and off; a rotatable tubular shaft having a first end and a second end, the rotatable tubular shaft operatively coupled to the rotatable acoustic valve at the first end and the binaural assembly at the second end; and a spring within the stethoscope chestpiece, wherein the spring prevents the rotatable tubular shaft from moving inside the chestpiece body. In this further embodiment, the rotatable acoustic valve is coupled to the positive adherent point element, the rotatable acoustic valve being configured to prevent an acoustic wave from traveling through the binaural assembly when the light emitting element is on.

In still a further embodiment, the second end of the rotatable tubular shaft is provided with a plurality of barbs for engaging the acoustic tube of the binaural assembly.

In yet a further embodiment, the power source of the power source subassembly is in the form of a battery for providing power to the light source subassembly, and wherein the power source subassembly further comprises: a positive adherent sheet, for creating an electrical current pathway from the power source to the light emitting element when operatively engaged with the positive connecting sheet; an insulating sheet, for preventing contact between the positive adherent sheet and the chestpiece body; and a pin positioned within the chestpiece body configured to prevent axial movement of the rotatable tubular shaft within the chestpiece body.

In still a further embodiment, a portion of the positive adherent sheet is disposed between the battery and the insulating sheet.

In yet a further embodiment, the rotatable tubular shaft comprises a circumferential groove disposed therein, the pin configured to engage with the circumferential groove of the rotatable tubular shaft.

In still a further embodiment, the rotatable acoustic valve is selectively positionable between a first closed position wherein the light emitting element is turned on and an acoustic passageway between the diaphragm and the acoustic tube is closed, and a second open position wherein the light emitting element is turned off and an acoustic passageway between the diaphragm and the acoustic tube is open so that sound waves are capable of being transmitted from the diaphragm to the acoustic tube of the binaural assembly.

In accordance with yet another aspect of one or more embodiments of the present invention, there is provided a stethoscope that includes a binaural assembly with an acoustic tube and a stethoscope chestpiece assembly. The stethoscope chestpiece assembly includes a chestpiece body having a first end and a second end; a diaphragm attached to the first end of the chestpiece body; a timepiece subassembly coupled to the chestpiece body, the timepiece subassembly configured to measure time during a vital sign examination; a power source subassembly including a power source, the power source subassembly operatively connected to the timepiece subassembly; and a rotatable acoustic valve disposed in the chestpiece body, the rotatable acoustic valve being fluidly coupled with the acoustic tube of the binaural assembly, and the rotatable acoustic valve being configured to regulate the transmission of sound waves through the binaural assembly.

In a further embodiment of this aspect of the present invention, the timepiece subassembly comprises: a timepiece mounted on the chestpiece body, the timepiece being powered by the power source subassembly.

In yet a further embodiment, the timepiece is in the form of a digital clock.

In still a further embodiment, the timepiece is in the form of an analog clock.

In accordance with still another aspect of one or more embodiments of the present invention, there is provided a stethoscope that includes a binaural assembly with an acoustic tube and a stethoscope chestpiece assembly. The stethoscope chestpiece assembly includes a chestpiece body having a first end and a second end; a diaphragm attached to the first end of the chestpiece body; a light source subassembly coupled to the chestpiece body, the light source subassembly including a light emitting element for performing a vital sign examination; a switch subassembly operatively coupled to the light source subassembly for turning the light emitting element on and off, the switch subassembly including a rotatable acoustic valve; a timepiece subassembly coupled to the chestpiece body, the timepiece subassembly configured to measure time during a vital sign examination; and a power source subassembly including a power source, the power source subassembly operatively connected to the timepiece subassembly and to the light source subassembly. In this embodiment, the rotatable acoustic valve is fluidly coupled with the acoustic tube of the binaural assembly, the rotatable acoustic valve being configured to regulate the transmission of sound waves through the binaural assembly.

In a further embodiment of this aspect of the present invention, the light source subassembly further comprises: a socket disposed within a cavity of the chestpiece body, the socket having a mouth; and a transparent dome-shaped cover disposed over the mouth of the socket. In this further embodiment, the light emitting element is disposed in the socket, the light emitting element configured to emit light in response to being energized by power supplied from the power source.

In yet a further embodiment, the switch subassembly comprises: a positive adherent point element coupled to a positive connecting sheet, the positive connecting sheet engageable with the power source subassembly for turning the light emitting element on and off; a rotatable tubular shaft having a first end and a second end, the rotatable tubular shaft operatively coupled to the rotatable acoustic valve at the first end and the binaural assembly at the second end; and a spring within the chestpiece, wherein the spring prevents the rotatable tubular shaft from moving inside the chestpiece body. In this further embodiment, the rotatable acoustic valve is coupled to the positive adherent point element, the rotatable acoustic valve being configured to prevent an acoustic wave from traveling through the binaural assembly when the light emitting element is on.

In still a further embodiment, the second end of the rotatable tubular shaft is provided with a plurality of barbs for engaging the acoustic tube of the binaural assembly.

In yet a further embodiment, the power source of the power source subassembly is in the form of a battery for providing power to the timepiece subassembly and the light source subassembly, and wherein the power source subassembly further comprises: a positive adherent sheet, for creating an electrical current pathway from the power source to the light emitting element when operatively engaged with the positive connecting sheet; an insulating sheet, for preventing contact between the positive adherent sheet and the chestpiece body; and a pin positioned within the chestpiece body configured to prevent axial movement of the rotatable tubular shaft within the chestpiece body.

In still a further embodiment, a portion of the positive adherent sheet is disposed between the battery and the insulating sheet.

In yet a further embodiment, the rotatable tubular shaft comprises a circumferential groove disposed therein, the pin configured to engage with the circumferential groove of the rotatable tubular shaft.

In still a further embodiment, the rotatable acoustic valve is selectively positionable between a first closed position wherein the light emitting element is turned on and an acoustic passageway between the diaphragm and the acoustic tube is closed, and a second open position wherein the light emitting element is turned off and an acoustic passageway between the diaphragm and the acoustic tube is open so that sound waves are capable of being transmitted from the diaphragm to the acoustic tube of the binaural assembly.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Throughout the figures, the same parts are always denoted using the same reference characters so that, as a general rule, they will only be described once.

DETAILED DESCRIPTION OF THE PREFERRED EMBODIMENT(S) OF THE INVENTION

The exemplary embodiment of the stethoscope assembly described below includes several integrated assemblies and subassemblies. One assembly is a chestpiece assembly with a chestpiece body and a diaphragm component securely attached to the chestpiece body. The chestpiece assembly also comprises a switch subassembly that is operatively connected to a light source subassembly for turning the light emitting element on and off. The switch subassembly further includes a rotatable acoustic valve that is operatively connected to a positive adherent point (i.e., a conductive element with a contact point or points) and allows a clinician to prevent the transmission of an acoustic wave from the diaphragm through the binaural assembly when the light source is on. The light source subassembly is secured to chestpiece body of the stethoscope and provides a practitioner with a practical medical device for a vital sign examination. The chestpiece assembly of the stethoscope also includes a timepiece subassembly which is secured to chestpiece body of the stethoscope and is configured to measure time during a vital sign examination. The light emitting element and the timepiece are powered by a battery. The stethoscope also includes a binaural assembly comprising an acoustic tube connected to an acoustic valve subassembly that allows patients' body sounds to travel from the diaphragm component to a practitioner's ear. The acoustic valve is a part of the switch subassembly and regulates auscultating as described hereinbelow.

Figure 1:
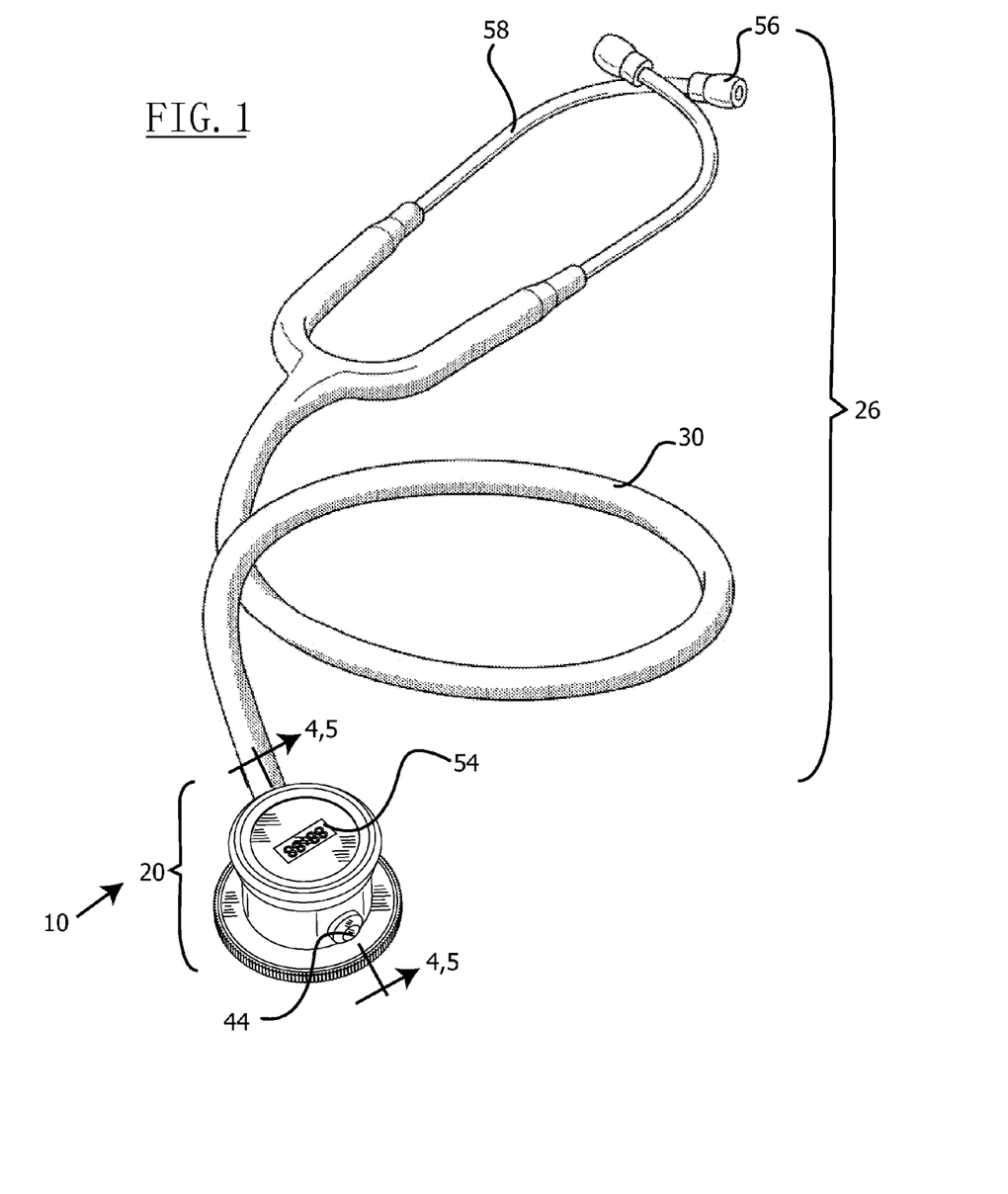
FIG. 1 is a perspective view of a stethoscope with a light source and a timepiece, according to an embodiment of the invention.

Referring now to the drawings and the reference characters marked thereon, and specifically to FIG. 1, stethoscope 10 made in accordance with an embodiment of the invention includes a chestpiece assembly 20 and a binaural assembly 26 that includes at least one earpiece 56. In the herein described embodiment of FIG. 1, the binaural assembly 26 includes two earpieces 56 wherein the depicted stethoscope 10 is a binaural stethoscope. As shown in FIG. 1, the binaural assembly 26 of the stethoscope 10 includes an acoustic tube 30 that is acoustically coupled to a headset with two (2) ear tubes 58. Each of the ear tubes 58 is provided with a respective earpiece 56 disposed on the end thereof.

Figure 3:
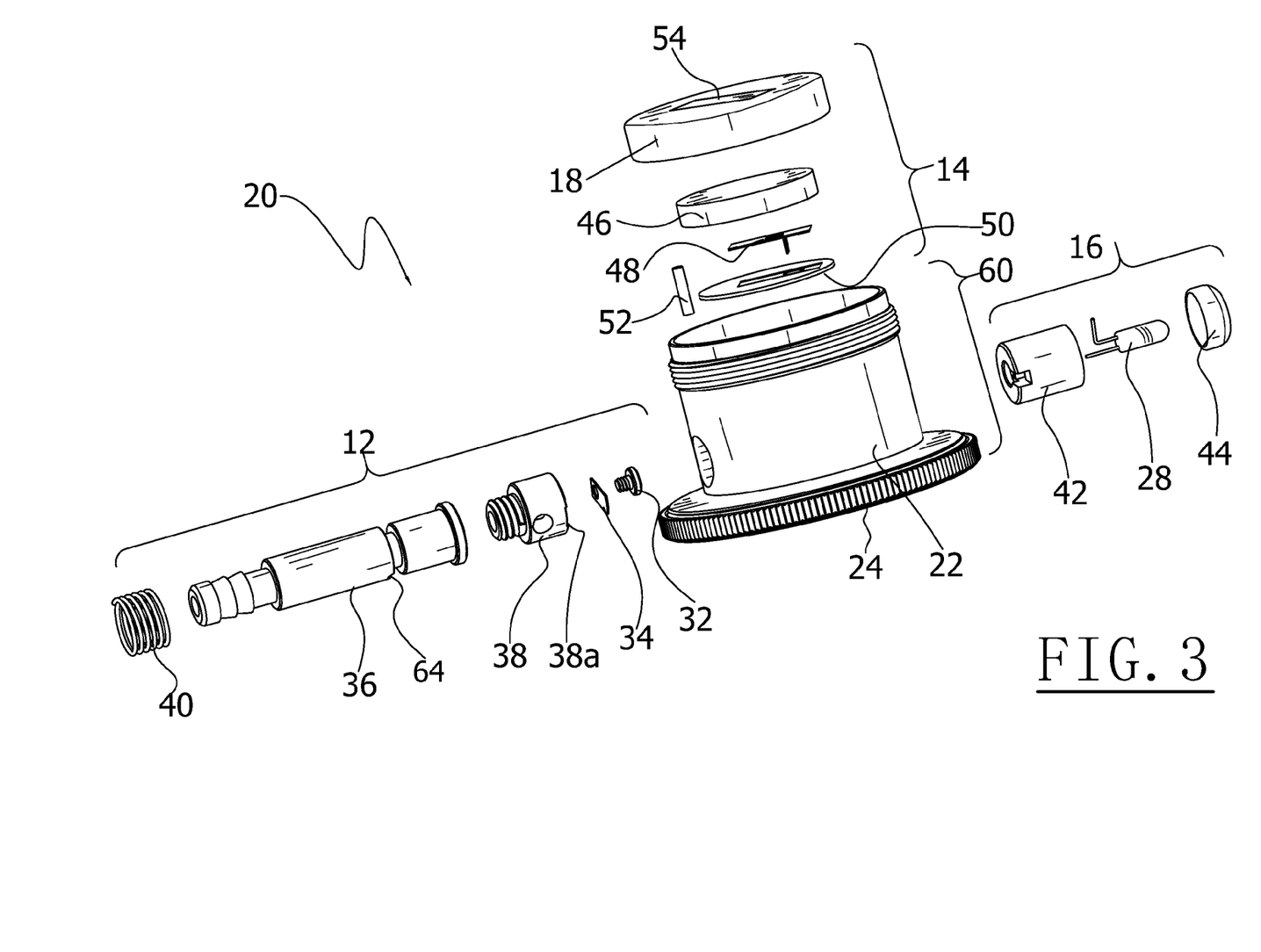
FIG. 3 is an exploded perspective view of the chestpiece assembly of the stethoscope, according to an embodiment of the invention.

FIG. 3 depicts an exploded view of the chestpiece assembly 20 of the stethoscope for proper physical examination of a patient, the stethoscope being designated generally as 10. The chestpiece assembly 20 includes a switch subassembly 12, a power source subassembly 14, a light source subassembly 16, a time piece subassembly 18, and a chestpiece body subassembly 60.

The chestpiece body subassembly 60 includes a chestpiece body 22 and a diaphragm component 24 which is securely attached to a first end of the chestpiece body 22 to intercept and amplify acoustic sounds of a patient during physical examination. The chestpiece body 22 is configured to transmit the acoustic sounds to the binaural assembly 26 shown in FIG. 1. The binaural assembly 26 includes an acoustic tube 30 which is connected to switch subassembly 12 with the rotatable acoustic valve 38.

The switch subassembly 12 that also operates as the valve of the sound is operably connected to the light source subassembly 16 to turn the light emitting element 28 on and off. The light source subassembly 16 is operatively connected to the chestpiece body 22 for allowing a practitioner to examine vital signs of a patient. The light source subassembly 16 includes a light emitting element 28.

In an exemplary embodiment, the light emitting element 28 is in the form of an incandescent, filament-type light bulb with an input voltage of approximately 3.0 volts (approximately 3.0 V) and an amperage of approximately 0.20 milliamps (approximately 0.20 mA). In an alternative embodiment, the light emitting element 28 is in the form of a light emitting diode (LED) light source. However, depending on its rated light output (e.g., in lumens), it is noted that an LED light source might be too bright for a patient's eye when a pupil reflex exam is being conducted using the stethoscope 10.

The timepiece subassembly 18 is securely connected to the second end of the chestpiece body 22 and is configured to measure time during a vital sign examination of a patient. The power source subassembly 14 is operatively connected to the timepiece subassembly 18 and to the light source subassembly 16 (i.e., it is electrically coupled to each of these subassemblies 16, 18), and thus, provides power to each of these two subassemblies 16, 18.

Figure 4:
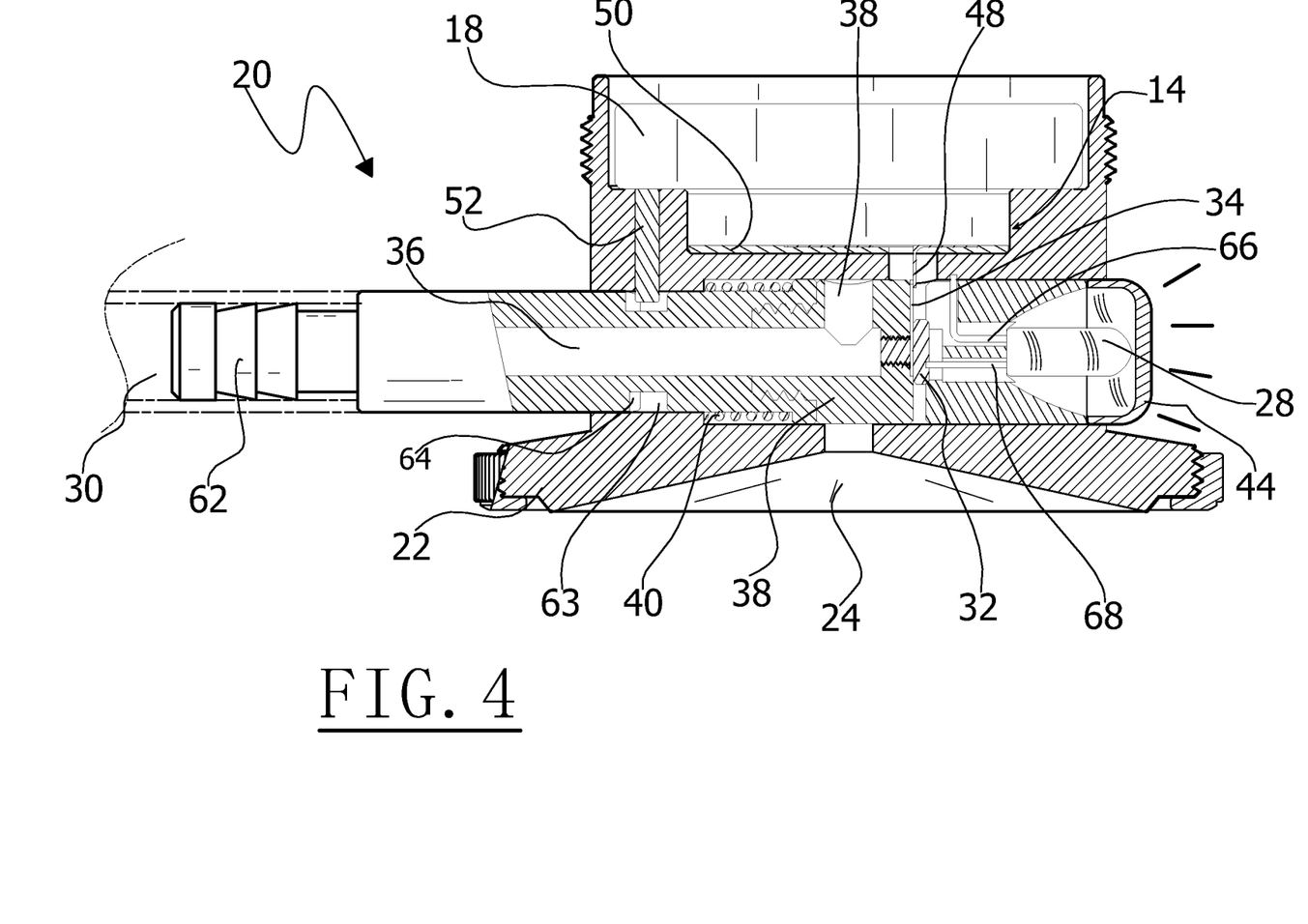
FIG. 4 is a cross-sectional view of the chestpiece assembly of the stethoscope cut along the cutting-plane line 4-4 in FIG. 1, wherein the light source is illustrated in an "on" position and the acoustic valve is in a closed position so as to prevent the transmission of sounds through the acoustic tube.
Figure 5:
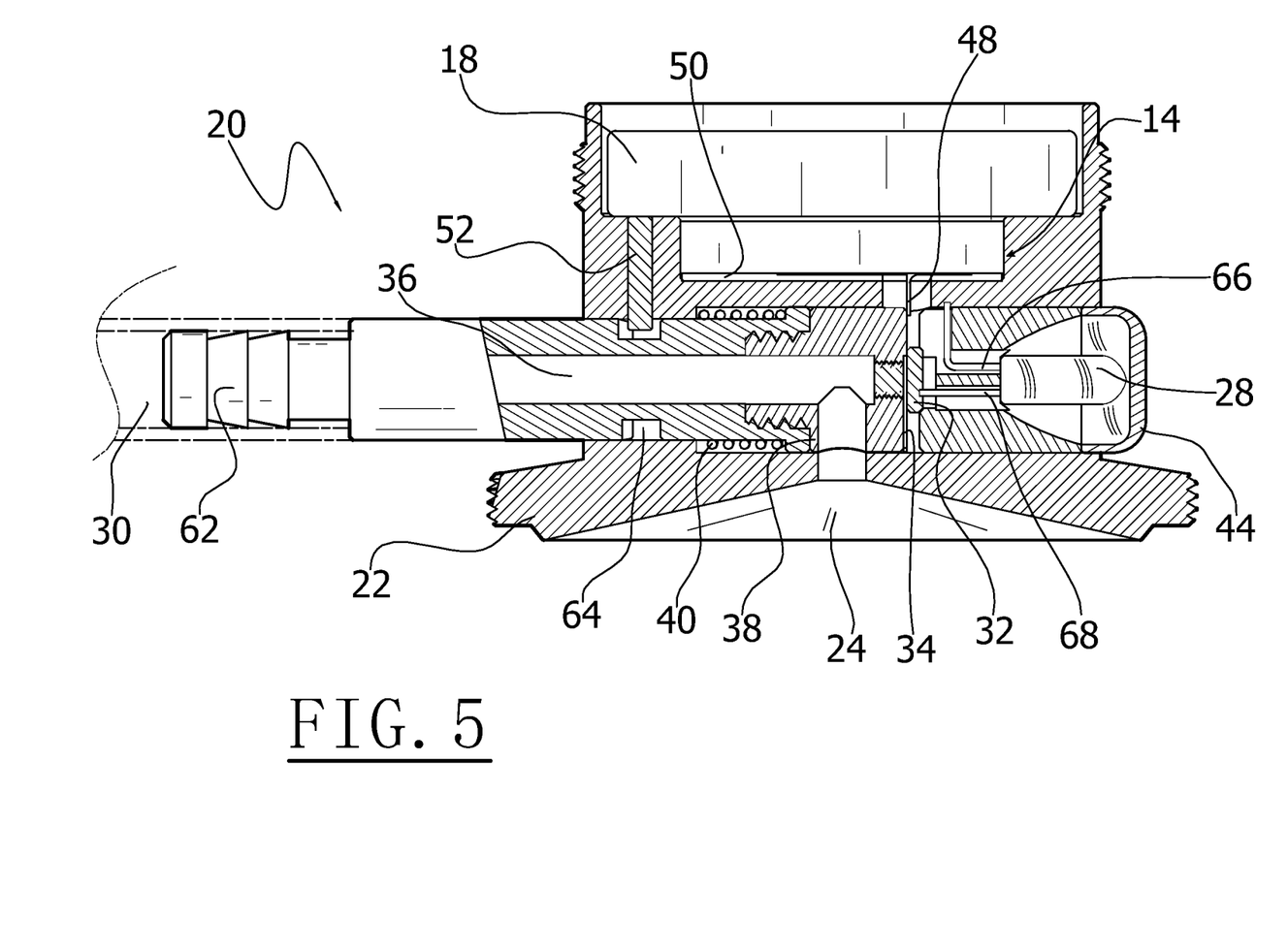
FIG. 5 is a cross-sectional view of the chestpiece assembly of the stethoscope cut along the cutting-plane line 5-5 in FIG. 1, wherein the light source is illustrated in an "off" position and the acoustic valve is in a open position so as to permit the transmission of sounds through the acoustic tube.

The switch subassembly 12 may include a positive adherent point element 32 (in the form of a conductive screw element, e.g., a metallic screw) that is operatively connected to a positive connecting sheet 34 (i.e., a generally planar conductive element 34 with an aperture disposed therein for receiving conductive screw element 32). As shown in FIG. 3, the end of the rotatable acoustic valve 38 is provided with a notch 38a disposed therein for receiving the positive connecting sheet 34 (conductive element 34). The positive connecting sheet 34 (conductive element 34) is configured to engage and disengage a positive adherent sheet 48 (i.e., a conductive element 48) of power source subassembly 14 as the rotating tubular shaft 36 of the switch subassembly 12 turns. The engagement and disengagement of the positive connecting sheet 34 (conductive element 34) of switch subassembly 12 and positive adherent sheet 48 (conductive element 48) of the power source subassembly 14 will selectively control an electrical current pathway for powering the light emitting element 28 on and off. When the positive connecting sheet 34 (conductive element 34) is engaged with the positive adherent sheet 48 (conductive element 48), an electrical current pathway is formed between the power source subassembly 14 and the light emitting element 28. In particular, as illustrated in FIGS. 4 and 5, the electrical lead 68 of the light emitting element 28 engages the conductive screw element 32 which, in turn, engages the conductive element 34 that engages conductive element 48. As also shown in FIGS. 4 and 5, the other electrical lead 66 of the light emitting element 28 engages an internal wall of the chestpiece body 22. Conversely, when the positive connecting sheet 34 (conductive element 34) is disengaged from the positive adherent sheet 48 (conductive element 48), the electrical current pathway between the power source subassembly 14 and the light emitting element 28 is interrupted (i.e., open circuit state) so as to prevent electrical current flow.

The switch subassembly 12 also includes a rotatable acoustic valve 38 which is configured to be operatively connected to the positive adherent point 32 (conductive screw element) for preventing an acoustic wave from traveling through the binaural assembly 26 when the light source is on.

The rotatable tubular shaft 36 of switch subassembly 12 is operatively connected to rotatable acoustic valve 38 at a first end and the binaural assembly 26 on a second end. In particular, as shown in FIG. 3, the rotatable acoustic valve 38 is provided with a plurality of external threads for matingly engaging with a plurality of internal threads in the first end of the rotatable tubular shaft 36. In addition, as shown in FIGS. 4 and 5, the second end of the rotatable tubular shaft 36 is provided with a barbed end 62 for securely engaging the end of the acoustic tube 30. The switch subassembly 12 may also include a spring 40 disposed within the chestpiece body 22 to prevent axial movement of the rotatable tubular shaft 36 inside the chestpiece body 22, and to facilitate engagement of the pin 52 with the notches 64 (i.e., the spring 40 applies an axial force to the rotatable tubular shaft 36 so that the pin 52 "clicks" into the notches 64). As such, by maintaining the pin 52 within one of the notches 64, the spring 40 prevents the rotatable tubular shaft 36 from inadvertently rotating out of one of its two operational positions, which are described hereinafter.

The light source subassembly 16 is configured to be connected to the chestpiece body 22. The light source subassembly 16 includes a socket 42 which is disposed within a cavity of the chestpiece body 22, where the socket has a mouth allowing the light emitting element 28 to be disposed in the socket 42 for emitting light in response to being energized by battery 46 of power source subassembly 14. The light source subassembly 16 also includes a transparent dome-like cover 44 which is disposed over the mouth of the socket 42.

The timepiece subassembly 18 includes a timepiece 54 which is mounted on the chestpiece body 22 and is powered by the battery 46 of power source subassembly 14. In an alternative embodiment, the timepiece subassembly 18 includes its own separate battery for powering the timepiece 54 within the housing of the timepiece subassembly 18. The timepiece subassembly may include a timepiece 54 that is a digital or analog clock.

Figure 2:
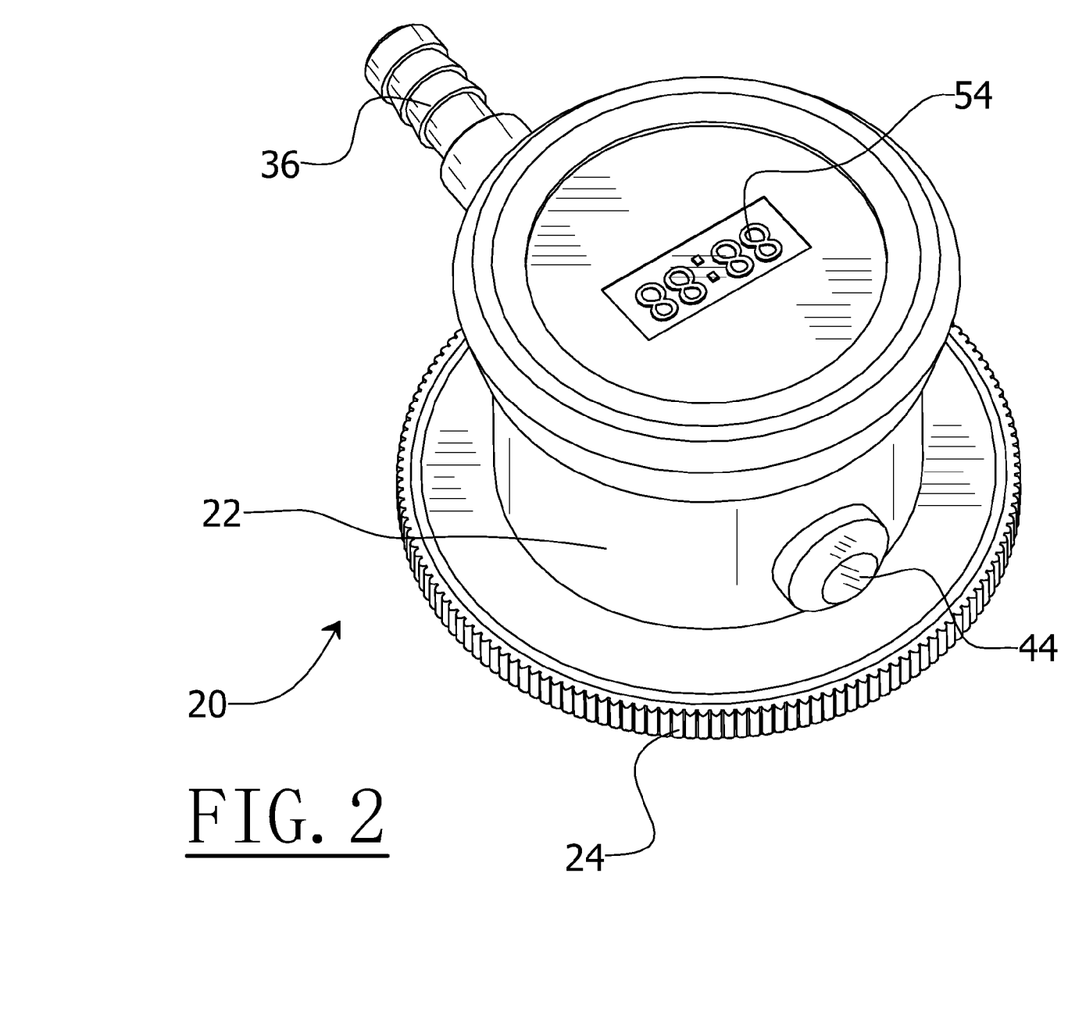
FIG. 2 is an assembled perspective view of the chestpiece assembly of the stethoscope, according to an embodiment of the invention.

As shown in FIGS. 1 and 2, in the illustrated embodiment, the timepiece 54 is provided with a digital display (e.g., a liquid crystal display (LCD) display). In an exemplary embodiment, the timepiece 54 has an input voltage of approximately 1.5 volts (approximately 1.5 V) and an amperage of approximately 0.07 milliamps (approximately 0.07 mA). However, it is to be understood that the timepiece 54 could be embodied in other suitable forms (e.g., an analog-type clock), and could have other suitable input voltages and amperages. While the timepiece 54 could be embodied as an analog movement-type clock, it is noted that such a movement-type clock could potentially cause noise in the chestpiece assembly 20, and thus, interfere with heart sounds.

The power source subassembly 14 includes a battery 46 for providing power to timepiece 54 of timepiece subassembly 18 and/or the light source subassembly 16 through the positive adherent sheet 48. An electrical current pathway is established from the battery 46 to the light emitting element 28 when positive adherent sheet 48 is operatively engaged with the positive connecting sheet 34. The power source subassembly 14 may also include an insulating sheet 50, for preventing contact between the positive adherent sheet 48 and the chestpiece body 22. In an exemplary embodiment, the battery 46 is in the form of a lithium button cell battery with an output voltage of approximately 3.0 volts (approximately 3.0 V) and an output amperage of approximately 0.20 milliamps (approximately 0.20 mA). However, it is to be understood that the battery 46 can be embodied in other suitable forms as well, with other suitable output voltages and currents.

The power source subassembly 14 also includes a rod or pin 52 positioned within the chestpiece body 22 which mainly restricts the axial movement of the rotatable tubular shaft 36 within the chestpiece body 22. As best shown in FIGS. 3-5, the circumferential groove 63 disposed about the periphery of the rotatable tubular shaft 36 (i.e., the acoustic valve stem) accommodates the pin 52, which holds the rotatable tubular shaft 36 in place. That is, the pin 52 is inserted through chestpiece body 22 into the circumferential groove 63 of the rotatable tubular shaft 36 so as to hold the rotatable tubular shaft 36 inside the chestpiece body 22. In addition, as depicted in FIGS. 3-5, there are two (2) small notches 64 in the groove 63 that are spaced approximately 180 degrees apart. Each of these two (2) notches 64 is configured to receive the pin 52 therein. These notches 64 give the user of the stethoscope 10 important tactile feedback for the proper first operational position (i.e., light "on" and acoustic valve "closed" position—FIG. 4) and the proper second operational position (i.e., light "off" and acoustic valve "open" position—FIG. 5 position). Without the tactile feedback afforded by the engagement between the pin 52 and each respective notch 64, it would be difficult for the user of the stethoscope 10 to find the proper rotational positions of the rotatable tubular shaft 36, which comprise each of these abovedescribed two operational states. As a result, without this tactile feedback, the user would most likely rotate the rotatable tubular shaft 36 to partially open and partially closed intermediate positions, which could compromise both the functionality of the light source subassembly 16 and the acoustical performance of the stethoscope 10.

Referring now to FIG. 4, the light emitting source 28 is shown in an "on" operating position. In this cross-sectional view of the chestpiece assembly 20 of the stethoscope 10, the positive adherent point element 32 of switch subassembly 12 is configured to operatively connect the positive connecting sheet 34 with the positive adherent sheet 48 of power source subassembly 14, to develop a current pathway resulting in turning the light emitting source 28 on. The engagement and disengagement of positive connecting sheet 34 of switch subassembly 12 with the positive adherent sheet 48 of power source subassembly 14 is controlled by the position of rotatable tubular shaft 36. Furthermore, rotatable acoustic valve 38 is configured with respect to the rotation of rotatable tubular shaft 36 to prevent body sounds of patients transmitted through the acoustic tube 30 when the light emitting source 28 is on.

FIG. 5 illustrates an exemplary embodiment of the chestpiece assembly 20 of the stethoscope 10 wherein the light emitting source 28 is in an "off" position. In this cross-sectional view of chestpiece body 22, the positive adherent point element 32 (conductive screw element) still contacts the electrical lead 68 of the light emitting element 28, but the positive connecting sheet 34 (conductive element), which is operatively connected to the positive adherent point element 32, is disengaged from the positive adherent sheet 48 (conductive element) of power source subassembly 14, thereby opening the electrical circuit and preventing electrical current flow to the light emitting element 28. This configuration is made possible by rotation of rotatable tubular shaft 36 of switch subassembly 12, furthermore positioning the rotatable acoustic valve 38 to be fluidly coupled with diaphragm component 24 allowing the patient's body sound to be intercepted, amplified and transmitted through the acoustic tube 30 and be heard by the practitioner. When the rotatable tubular shaft 36 of switch subassembly 12 is rotated 180 degrees by the user of the stethoscope 10 (i.e., by the user grasping the portion of the rotatable tubular shaft 36 that is disposed externally from the chestpiece body 22 and twisting it—see FIGS. 2, 4, and 5), the positive connecting sheet 34 (conductive element) is simultaneously rotated along with the rotatable tubular shaft 36 from the position of FIG. 5 to the position of FIG. 4. In the FIG. 4 position, as described above, the positive connecting sheet 34 (conductive element) engages the positive adherent sheet 48 (conductive element) so as to form an electrical current pathway between the power source subassembly 14 and the light emitting element 28, thereby turning the light "on".

It is readily apparent that the aforedescribed inventive stethoscope 10 offers numerous advantages. First, the stethoscope 10 includes a plurality of devices that could be utilized by a medical practitioner to conduct a proper vital sign examination of a patient in a timely manner. In particular, when used in conjunction with a sphygmomanometer, the stethoscope 10 allows clinicians to properly check four (4) out the five (5) primary vital signs. The stethoscope 10 of the aforedescribed embodiment combines many of the major tools (i.e., a stethoscope, light and timepiece) required for a vital sign examination, thereby enabling clinicians to properly conduct their vital sign examinations. By virtue of its timepiece, the inventive stethoscope 10 allows measurement of respiratory rate and heart rate by a clinician. Moreover, the stethoscope 10 permits a clinician to check a plurality of the patient's vital signs without necessitating the removal of the instrument. Specifically, the novel switch subassembly 12 of the stethoscope 10 allows auscultating while the physician is able to keep the ear-tips inside his or her ear. Furthermore, the stethoscope 10 allows a clinician to turn off the sound and use the light for a pupil exam without removing the headset. The switch subassembly 12 of the stethoscope 10 provides a safety mechanism for clinicians by prohibiting the transmission of a loud sound if the chestpiece accidently knocks against a non-human object. Advantageously, the features of the inventive stethoscope 10 give the clinician the flexibility to use all three tools at once without having to remove the headset if, for example, the clinician wants to auscultate once again.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A stethoscope, comprising:
a binaural assembly including an acoustic tube; and
a stethoscope chestpiece assembly including:
a chestpiece body having a first end and a second end;
a diaphragm attached to said first end of said chestpiece body;
a light source subassembly coupled to said chestpiece body, said light source subassembly including a light emitting element for performing a vital sign examination;
a switch subassembly operatively coupled to said light source subassembly for turning said light emitting element on and off, said switch subassembly including a rotatable acoustic valve, said switch subassembly further including a positive adherent point element coupled to a positive connecting sheet, said positive connecting sheet engageable with said power source subassembly for turning said light emitting element on and off; a rotatable tubular shaft having a first end, a second end, and a circumferential groove disposed therein, said rotatable tubular shaft operatively coupled to said rotatable acoustic valve at said first end and said binaural assembly at said second end; and a spring within said stethoscope chestpiece, wherein said spring prevents said rotatable tubular shaft from moving inside said chestpiece body; and
a power source subassembly including a power source, said power source subassembly operatively connected to said light source subassembly, said power source of said power source subassembly being in the form of a battery for providing power to light emitting element of said light source subassembly, said power source subassembly further including a positive adherent sheet for creating an electrical current pathway from said power source to said light emitting element when operatively engaged with said positive connecting sheet; an insulating sheet for preventing contact between said positive adherent sheet and said chestpiece body; and a pin positioned within said chestpiece body configured to prevent axial movement of said rotatable tubular shaft within said chestpiece body, said pin configured to engage with said circumferential groove of said rotatable tubular shaft;

wherein said rotatable acoustic valve is fluidly coupled with said acoustic tube of said binaural assembly, said rotatable acoustic valve being configured to regulate the transmission of sound waves through said binaural assembly; and wherein said rotatable acoustic valve is coupled to said positive adherent point element, said rotatable acoustic valve being configured to prevent an acoustic wave from traveling through said binaural assembly when said light emitting element is on.

2. The stethoscope according to claim 1, wherein said light source subassembly further comprises:
   a socket disposed within a cavity of said chestpiece body, said socket having a mouth; and
   a transparent dome-shaped cover disposed over said mouth of said socket;
   wherein said light emitting element is disposed in said socket, said light emitting element configured to emit light in response to being energized by power supplied from said power source.

3. The stethoscope according to claim 1, wherein said second end of said rotatable tubular shaft is provided with a plurality of barbs for engaging said acoustic tube of said binaural assembly.

4. The stethoscope according to claim 1, wherein a portion of said positive adherent sheet is disposed between said battery and said insulating sheet.

5. The stethoscope according to claim 1, wherein said rotatable acoustic valve is selectively positionable between a first closed position wherein said light emitting element is turned on and an acoustic passageway between said diaphragm and said acoustic tube is closed, and a second open position wherein said light emitting element is turned off and an acoustic passageway between said diaphragm and said acoustic tube is open so that sound waves are capable of being transmitted from said diaphragm to said acoustic tube of said binaural assembly.

6. The stethoscope according to claim 1, wherein said rotatable valve has a first end and a second end, said first end of said rotatable valve being disposed opposite to said second end of said rotatable valve; and
   wherein said positive adherent point element is in the form a screw, said positive adherent point element being attached to said first end of said rotatable acoustic valve, and said second end of said rotatable acoustic valve being attached to said first end of said rotatable tubular shaft.

7. The stethoscope according to claim 6, wherein said positive connecting sheet is attached to said first end of said rotatable acoustic valve by means of said positive adherent point element.

8. A stethoscope, comprising:
   a binaural assembly including an acoustic tube; and
   a stethoscope chestpiece assembly including:
      a chestpiece body having a first end and a second end;
      a diaphragm attached to said first end of said chestpiece body;
      a timepiece subassembly coupled to said chestpiece body, said timepiece subassembly configured to measure time during a vital sign examination;
      a power source subassembly including a power source, said power source subassembly operatively connected to said timepiece subassembly;
      a rotatable acoustic valve disposed in said chestpiece body, said rotatable acoustic valve being fluidly coupled with said acoustic tube of said binaural assembly, said rotatable acoustic valve being configured to regulate the transmission of sound waves through said binaural assembly;
      a rotatable tubular shaft having a first end, a second end, and a circumferential groove disposed therein, said rotatable tubular shaft operatively coupled to said rotatable acoustic valve at said first end and said binaural assembly at said second end; and
      a pin having a linear body with a first end and a second end, said linear body of said pin extending from said first end proximate to said timepiece subassembly to said second end disposed in said circumferential groove of said rotatable tubular shaft, said pin being stationarily disposed within an aperture of said chestpiece body and being configured to prevent an axial movement of said rotatable tubular shaft within said chestpiece body by engaging with said circumferential groove of said rotatable tubular shaft, said rotatable tubular shaft and said rotatable acoustic valve being configured to rotate together relative to said pin.

9. The stethoscope according to claim 8, wherein said timepiece subassembly comprises:
   a timepiece mounted on said chestpiece body, said timepiece being powered by said power source subassembly.

10. The stethoscope according to claim 9, wherein said timepiece is in the form of a digital clock.

11. The stethoscope according to claim 9, wherein said timepiece is in the form of an analog clock.

12. The stethoscope according to claim 8, wherein said timepiece subassembly comprises a timepiece mounted on said chestpiece body, said timepiece being powered by said power source subassembly; and wherein said pin is disposed between said timepiece and said rotatable tubular shaft.

13. The stethoscope according to claim 8, wherein said timepiece subassembly comprises a timepiece mounted on said chestpiece body, and wherein said power source of said power source subassembly is in the form of a battery for providing power to said timepiece of said timepiece subassembly, said battery being disposed between said timepiece and said rotatable acoustic valve.

14. A stethoscope, comprising:
   a binaural assembly including an acoustic tube; and
   a stethoscope chestpiece assembly including:
      a chestpiece body having a first end and a second end;
      a diaphragm attached to said first end of said chestpiece body;
      a light source subassembly coupled to said chestpiece body, said light source subassembly including a light emitting element for performing a vital sign examination;
      a switch subassembly operatively coupled to said light source subassembly for turning said light emitting element on and off, said switch subassembly including a rotatable acoustic valve, said switch subassembly further including a positive adherent point element coupled to a positive connecting sheet, said positive connecting sheet engageable with said power source subassembly for turning said light emitting element on and off; a rotatable tubular shaft having a first end, a second end, and a circumferential groove disposed therein, said rotatable tubular shaft operatively coupled to said rotatable acoustic valve at said first end and said binaural assembly at said second end; and a spring within said stethoscope chestpiece, wherein said spring prevents said rotatable tubular shaft from moving inside said chestpiece body;

a timepiece subassembly coupled to said chestpiece body, said timepiece subassembly comprising a timepiece configured to measure time during a vital sign examination; and a power source subassembly including a power source, said power source subassembly operatively connected to said timepiece subassembly and to said light source subassembly, said power source of said power source subassembly being in the form of a battery for providing power to said timepiece of said timepiece subassembly and said light emitting element of said light source subassembly, said power source subassembly further including a positive adherent sheet for creating an electrical current pathway from said power source to said light emitting element when operatively engaged with said positive connecting sheet; an insulating sheet for preventing contact between said positive adherent sheet and said chestpiece body; and a pin positioned within said chestpiece body configured to prevent axial movement of said rotatable tubular shaft within said chestpiece body, said pin configured to engage with said circumferential groove of said rotatable tubular shaft;

wherein said rotatable acoustic valve is fluidly coupled with said acoustic tube of said binaural assembly, said rotatable acoustic valve being configured to regulate the transmission of sound waves through said binaural assembly; and wherein said rotatable acoustic valve is coupled to said positive adherent point element, said rotatable acoustic valve being configured to prevent an acoustic wave from traveling through said binaural assembly when said light emitting element is on.

15. The stethoscope according to claim 14, wherein said light source subassembly further comprises:

a socket disposed within a cavity of said chestpiece body, said socket having a mouth; and a transparent dome-shaped cover disposed over said mouth of said socket;

wherein said light emitting element is disposed in said socket, said light emitting element configured to emit light in response to being energized by power supplied from said power source.

16. The stethoscope according to claim 14, wherein said second end of said rotatable tubular shaft is provided with a plurality of barbs for engaging said acoustic tube of said binaural assembly.

17. The stethoscope according to claim 14, wherein a portion of said positive adherent sheet is disposed between said battery and said insulating sheet.

18. The stethoscope according to claim 14, wherein said rotatable acoustic valve is selectively positionable between a first closed position wherein said light emitting element is turned on and an acoustic passageway between said diaphragm and said acoustic tube is closed, and a second open position wherein said light emitting element is turned off and an acoustic passageway between said diaphragm and said acoustic tube is open so that sound waves are capable of being transmitted from said diaphragm to said acoustic tube of said binaural assembly.

19. The stethoscope according to claim 14, wherein said rotatable valve has a first end and a second end, said first end of said rotatable valve being disposed opposite to said second end of said rotatable valve; and wherein said positive adherent point element is in the form a screw, said positive adherent point element being attached to said first end of said rotatable acoustic valve, and said second end of said rotatable acoustic valve being attached to said first end of said rotatable tubular shaft.

20. The stethoscope according to claim 19, wherein said positive connecting sheet is attached to said first end of said rotatable acoustic valve by means of said positive adherent point element.

* * * * *